United States Patent [19]

Schramm et al.

[11] Patent Number: 5,507,298
[45] Date of Patent: Apr. 16, 1996

[54] FORWARD-FIRED AUTOMATIC TISSUE SAMPLING APPARATUS

[75] Inventors: John B. Schramm; Manfred Mittermeier, both of Skokie; Alan Hable, Schiller Park, all of Ill.

[73] Assignee: M3 Systems, Inc., d/b/a/ Manan Medical Products, Inc., Northbrook, Ill.

[21] Appl. No.: 311,507

[22] Filed: Sep. 23, 1994

[51] Int. Cl.⁶ .................................................. A61B 10/00
[52] U.S. Cl. ................................................ 128/754
[58] Field of Search ..................... 128/749, 751–754; 606/167, 170

[56] References Cited

U.S. PATENT DOCUMENTS

| | | | |
|---|---|---|---|
| Re. 34,056 | 9/1992 | Lindgren et al. | 128/754 |
| 4,461,305 | 7/1984 | Cibley | 128/754 |
| 4,594,073 | 6/1986 | Stine | 604/187 |
| 4,600,014 | 7/1986 | Beraha | 128/754 |
| 4,699,154 | 10/1987 | Lindgren | 128/754 |
| 4,735,215 | 4/1988 | Goto et al. | 128/754 |
| 4,738,664 | 4/1988 | Prindle | 604/228 |
| 4,747,831 | 5/1988 | Kulli | 604/110 |
| 4,766,907 | 8/1988 | de Groot et al. | 128/754 |
| 4,776,346 | 10/1988 | Beraha et al. | 128/754 |
| 4,907,599 | 3/1990 | Taylor | 128/754 |
| 4,917,100 | 4/1990 | Nottke | 128/749 |
| 4,944,308 | 7/1990 | Akerfeldt | 128/754 |
| 4,953,558 | 9/1990 | Akerfeldt | 128/751 |
| 4,958,625 | 9/1990 | Bates et al. | 128/754 |
| 4,986,278 | 1/1991 | Ravid et al. | 128/753 |
| 5,121,751 | 6/1992 | Panalletta | 128/754 |
| 5,172,701 | 12/1992 | Leigh | 128/753 |
| 5,172,702 | 12/1992 | Leigh et al. | 128/754 |
| 5,188,118 | 2/1993 | Terwilliger | 128/754 |
| 5,224,470 | 7/1993 | Schnepp-Pesch et al. | 128/754 |
| 5,284,156 | 2/1994 | Schramm et al. | 128/754 |
| 5,348,022 | 9/1994 | Leigh et al. | 128/753 |

FOREIGN PATENT DOCUMENTS

| | | |
|---|---|---|
| 0010321 | 4/1980 | European Pat. Off. . |
| 483829 | 2/1970 | Switzerland . |
| WO83/03343 | 10/1983 | WIPO . |
| WO88/07839 | 10/1988 | WIPO . |

OTHER PUBLICATIONS

Article–"Percutaneous Needle Biopsy–A new technique". *Acta Radiologica Diagnosis* 23(1982) pp. 653–656 by P. G. Lindgren.

*Primary Examiner*—Max Hindenburg
*Attorney, Agent, or Firm*—Dick and Harris

[57] ABSTRACT

An apparatus for the automated and facilitated handling and operation of a biopsy needle system, having a first needle component and a second needle component. The first and second needles are provided with first and second handles, respectively, which are fitted into first and second yokes of the apparatus. The apparatus is configured to maintain the first and second needles in a first position, during insertion of the biopsy needle point into the tissue being sampled. The apparatus is further configured to forwardly move the first and second needles into subsequent positions, respectively, in rapid, automated succession so as to segment and enclose a tissue sample, which may be tested after removal of the biopsy needle system from the tissue. A tissue sample inspection feature permits facilitated repositioning and maintenance of the first needle relative to the second needle after retrieval of the tissue sample to, in turn, enable inspection of the retrieved tissue sample without removal of either needle from the apparatus. The apparatus is further configured so as to be actuatable from positions adjacent the front or the rear of the apparatus housing.

19 Claims, 6 Drawing Sheets

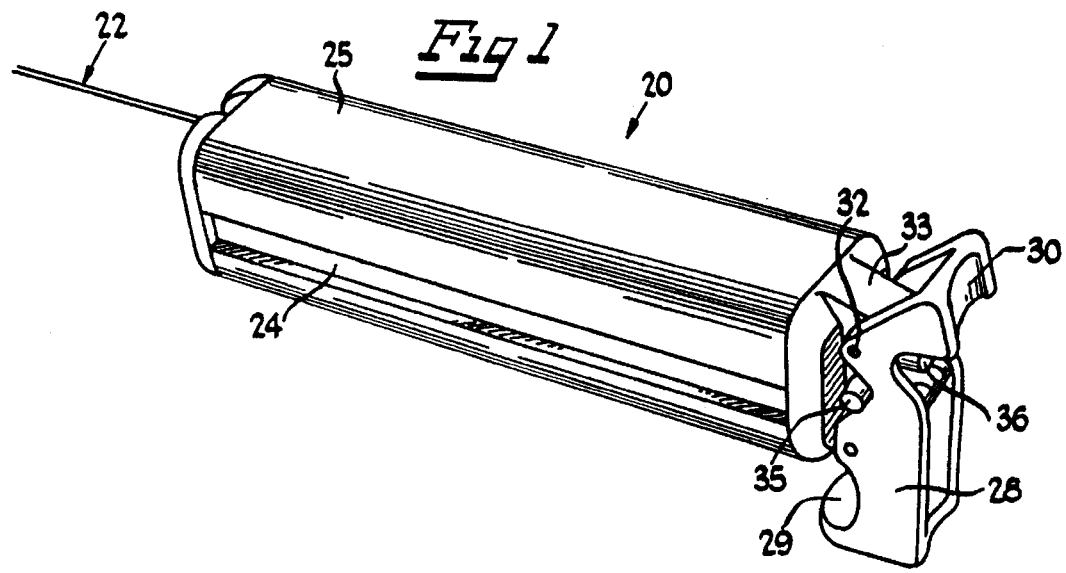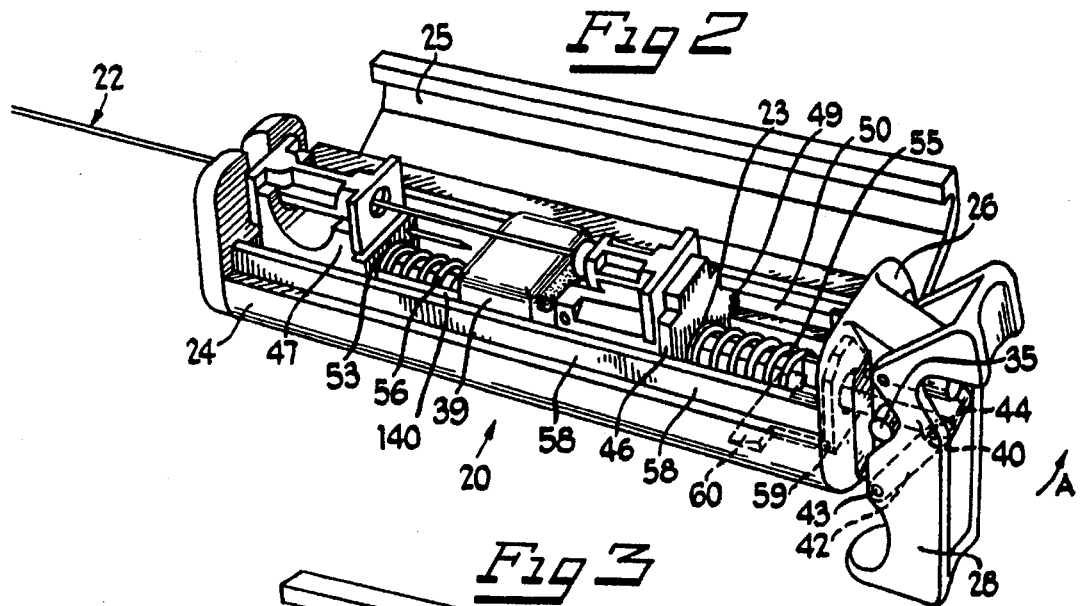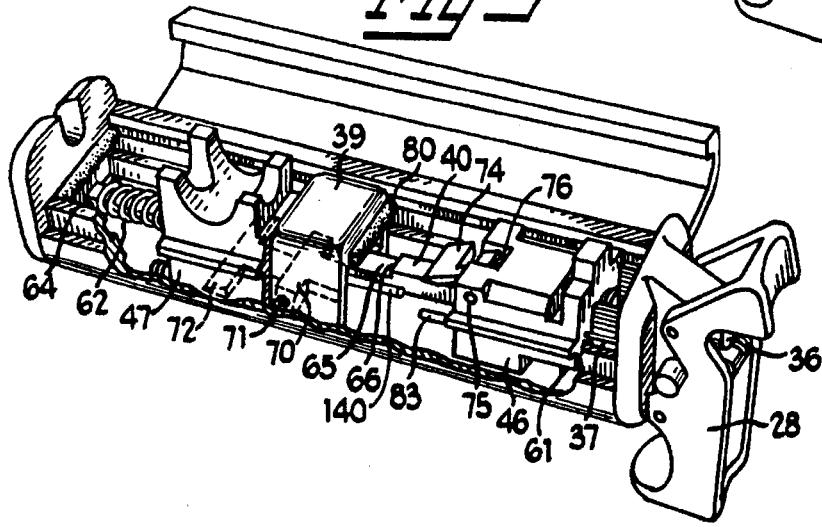

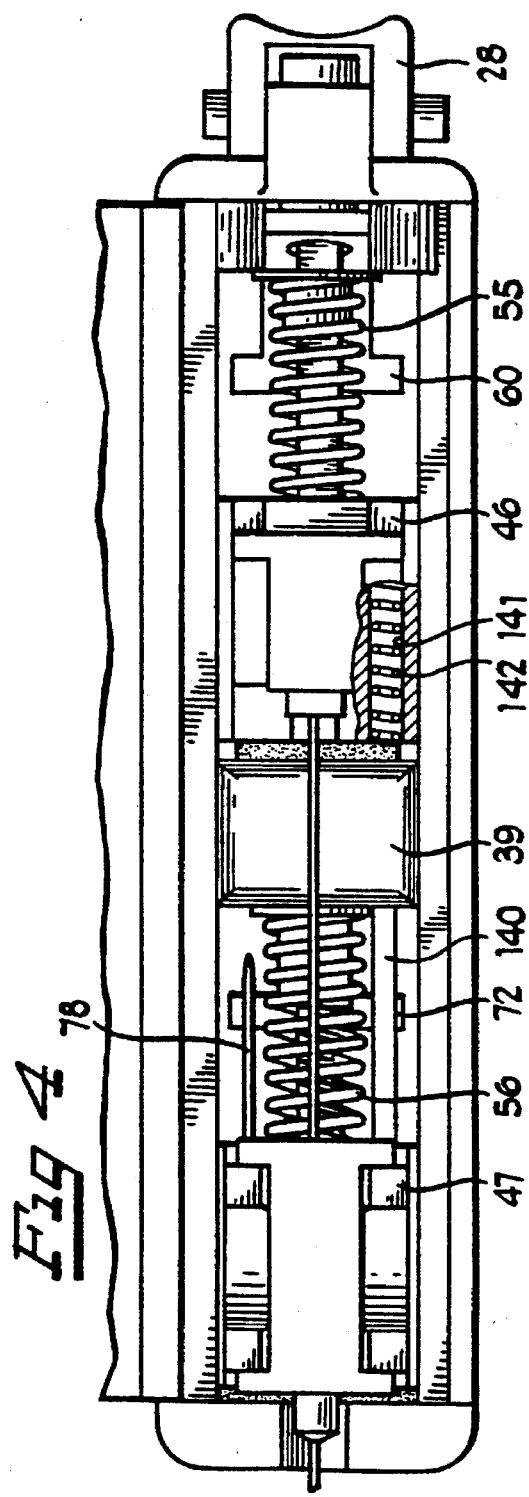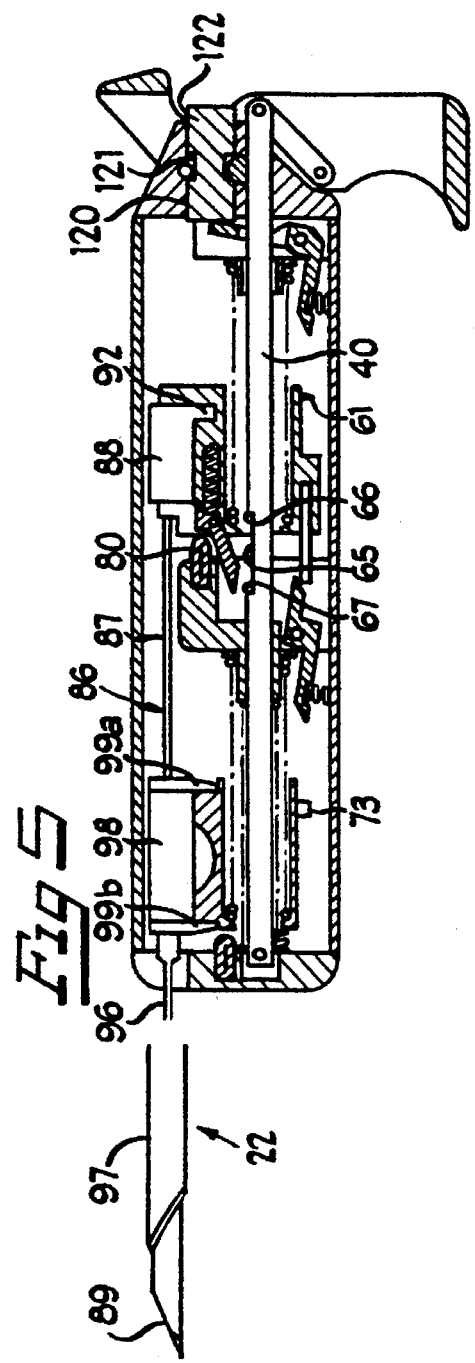

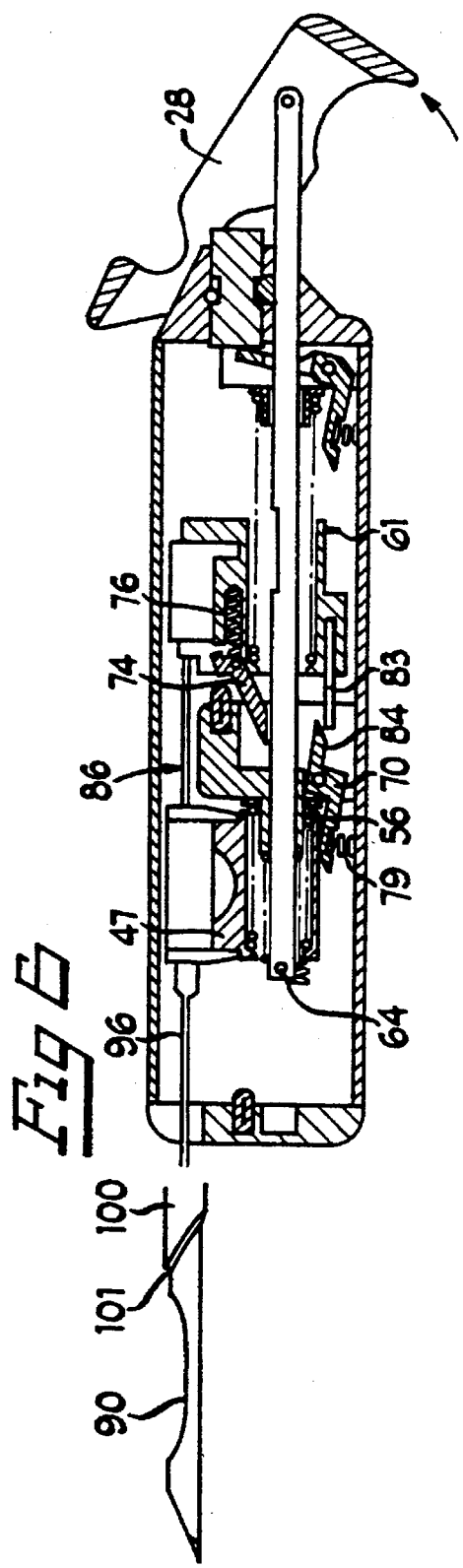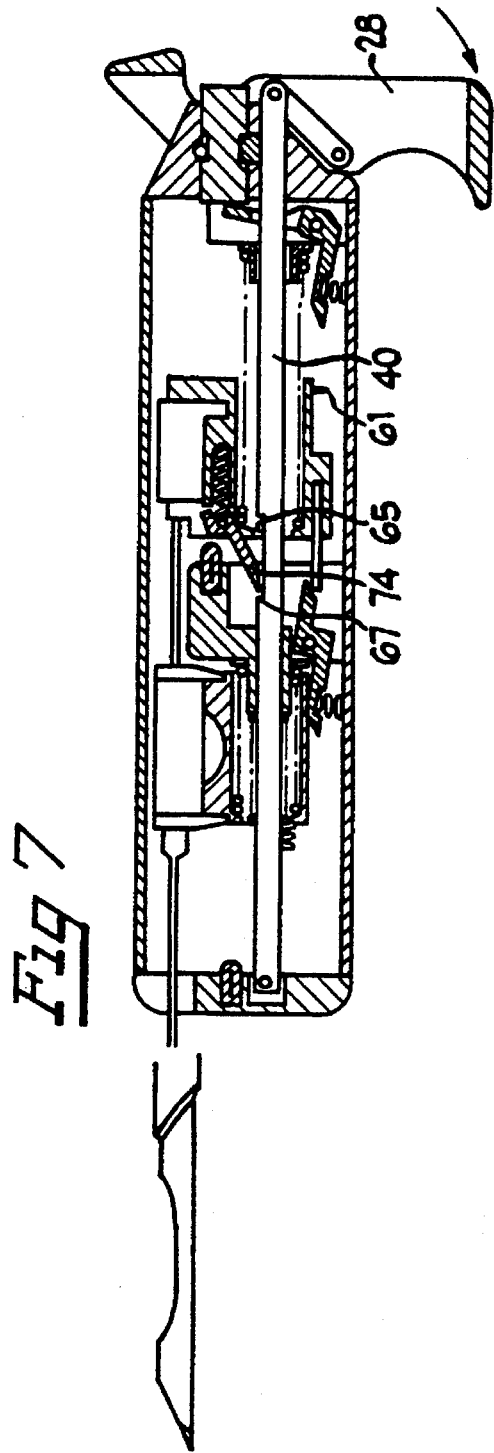

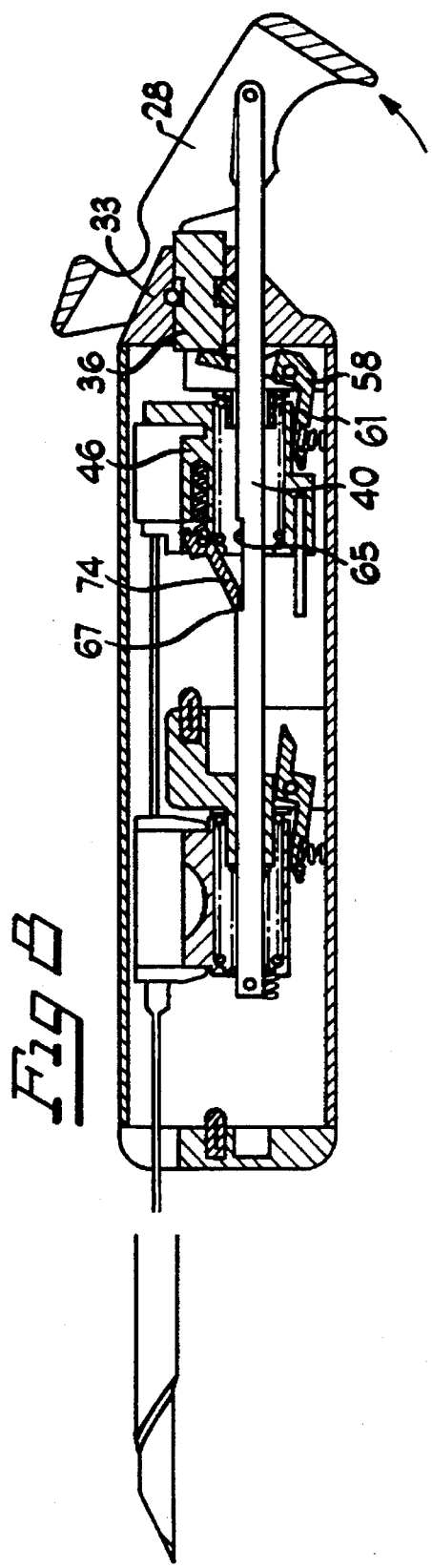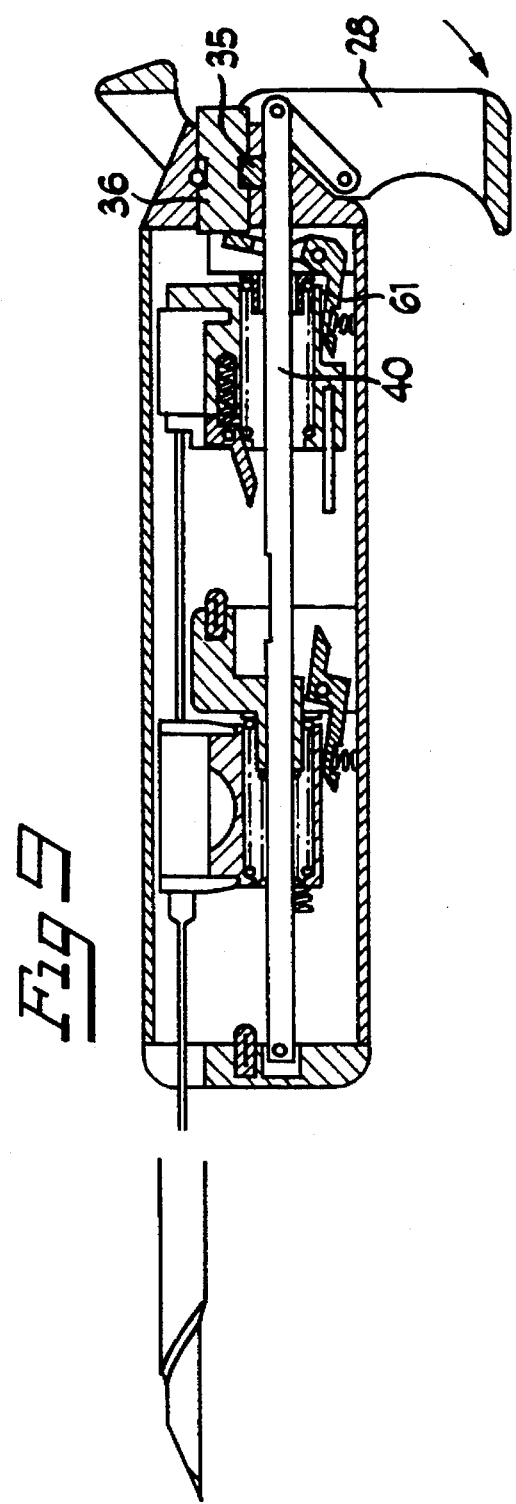

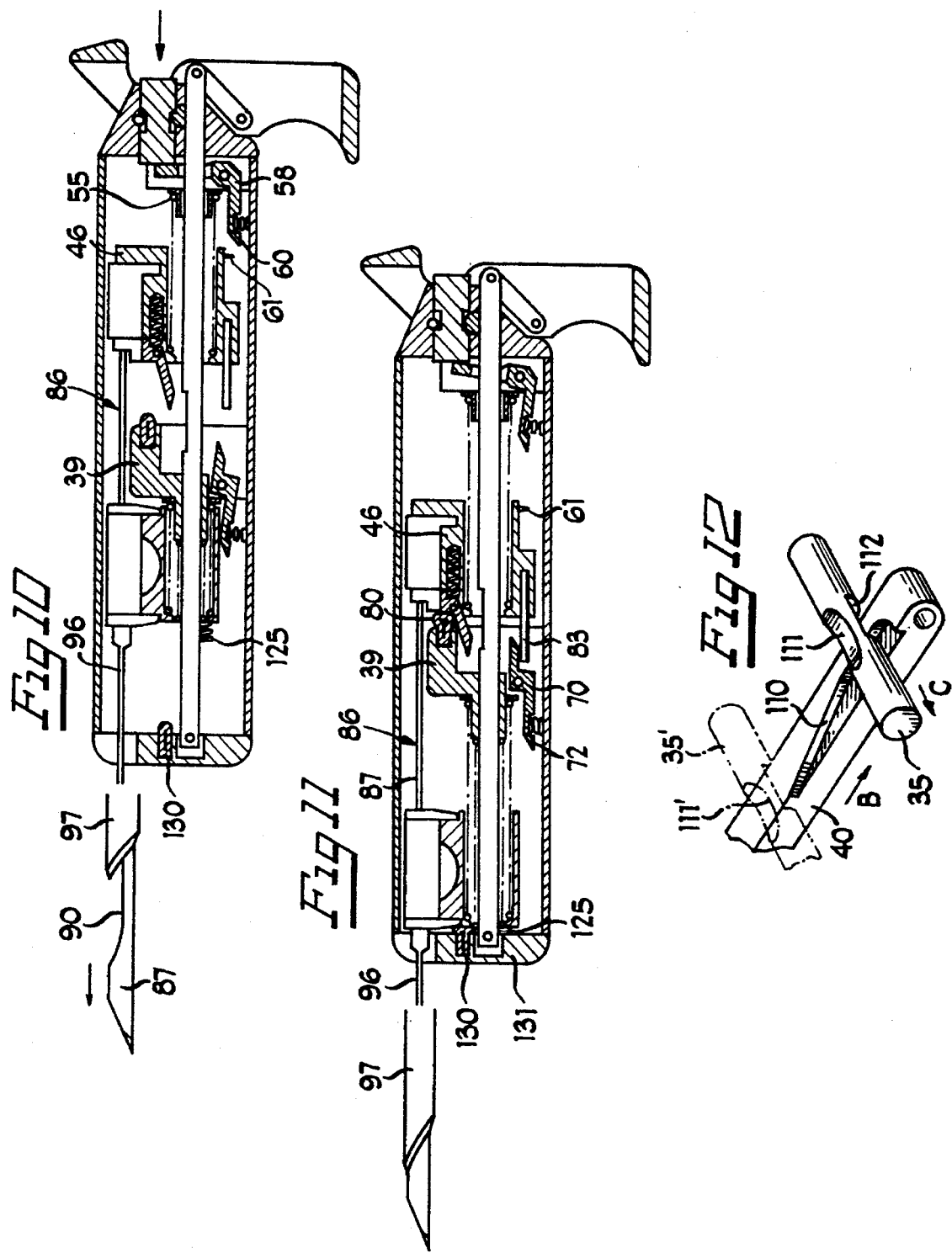

FORWARD-FIRED AUTOMATIC TISSUE SAMPLING APPARATUS

BACKGROUND OF THE INVENTION

The present invention relates to tissue sampling devices associated with biopsy needles, and in particular, to an automatic tissue sampling apparatus for utilizing two-piece biopsy needle systems for facilitating the retrieval of a tissue sample for testing.

A typical biopsy needle system utilized in obtaining tissue samples is composed of two parts, a first needle and a second needle. The first needle consists of a substantially solid shaft, having a first handle disposed at one end. A cutting point, to facilitate insertion of the needle into the tissue to be sampled, is located at the other end of the shaft, opposite to the position of the handle. Positioned proximate to the cutting point is a tissue holding region, which is in the form of a cut-out region or flat in the otherwise substantially cylindrical shaft.

The second needle is typically hollow, and has a cutting point disposed at one end. At the other end, a second handle is disposed. The hollow passageway extends through the second handle, to enable the solid shaft of the first needle to be inserted into the passageway and into and through the entire hollow shaft of the second needle.

The shaft of the first, inner, solid needle is typically greater in length than the entire second, outer, hollow needle structure. When the first and second handles are placed in a particularly spaced co-axial configuration, the hollow shaft of the second needle covers the tissue holding region of the first needle. The tissue holding region may be exposed by projecting the first needle further into the second needle, bringing the first and second handles closer together.

To obtain a tissue sample, the biopsy needle system is typically inserted into a patient, into the specific tissue to be sampled, at the desired cell mass to be investigated, with the first and second needles relatively positioned in the first described configuration, so that the tissue holding region is covered. The tissue holding region is then exposed, by the operator holding the second handle of the second needle stable while projecting the first needle forward a short distance along its sharp pointed region-until a portion of the tissue being tested surrounds the flat cut-out of the tissue holding region.

The second needle, which also has a sharp, though hollow, point disposed at the end of the hollow shaft opposite the second handle, is then moved forward, relative to the now-stabilized first needle—to cut off the tissue sample from the rest of the tissue, and cover the tissue sample about the flat cut-out of the tissue holding region. The angled cutting point of the second needle serves to sever the tissue sample. The first and second needles are typically maintained in a particular angular concentric orientation with respect to one another, prior to insertion, so as to maintain the forwardmost portion of the second needle point centered when positioned over the flat, cut-out region of the first needle.

After the tissue is severed and confined between the first and second needles, the first and second needles will be brought back to the same relative positions they occupied immediately prior to initial insertion of the biopsy needle system into the patient. To prevent loss or contamination of the tissue sample, the first and second needles are typically removed from the patient in this tissue-isolating configuration.

As the configuration of the first and second needles, utilized for initial insertion, and final removal from the patient, requires that the first and second handles be spaced apart in a particular configuration, the manual manipulation of such a biopsy needle system requires considerable dexterity, concentration and skill on the part of the operator. The concentration necessary to maintain the proper spacing may detract from the concentration necessary to make insertion and removal of the biopsy needle as painless as possible for the patient. Accordingly, it is desirable to provide a form of automatic tissue sampling apparatus, which accomplishes some, if not all of the handling steps just described—so that the operator may be concerned with the crucial initial step of insertion and final step of removal, of the biopsy needle system; to reduce the amount of discomfort to the patient, to improve the quality of the results of the tissue sampling procedure, and to enhance the successful repeatability of the procedure, from one patient to the next.

Examples of prior art automatic tissue sampling apparatus include those disclosed in PCT application No. PCT/SE83/00112, Swedish Patent No. 8600755, U.S. Pat. No. 4,699,154, issued to Lindgren, U.S. Pat. Nos. 4,944,308, and 4,953,558, issued to Akerfeldt, EPO Application No. 0 318 447 and Swiss Patent No. 483 829.

In the PCT '00112 application, an automatic tissue sampling apparatus is disclosed, in which the first needle of the biopsy needle system is propelled forward by a pressure plate which is driven by a compressed spring, and the second needle is propelled by a movable slide which receives the second handle of the second needle. The movable slide for holding the second needle is also propelled by a compressed spring. In order to prepare the apparatus for use, each of the springs and respective slides must be cocked separately, either manually or through the use of a specially shaped tool. The slide for the second handle is held in place by a catch which is configured to be released upon contact with a projection arranged upon the slide for the first handle of the first needle. The pressure plate for the first handle of the first needle is, in turn, retained in its cocked position by a trigger which is actuatable by the operator. While it is possible to cock each of the spring with the biopsy needle already in place, it is contemplated that such cocking could take place well prior to loading of the needle.

In the operation of the PCT '00112 device, once the springs have been cocked and the biopsy needle system has been loaded (either before or after cocking), the operator inserts the biopsy needle system into the tissue to be sampled, as previously described. He or she may then depress the trigger which releases the spring for propelling the first needle. As the first needle is moved forward, the pressure plate releases the retaining mechanism which has been previously holding the movable slide for the second handle of the second needle. The second needle is thus moved forward shortly after the first needle, completing the sampling movement. The trigger in the apparatus is biased by a spring into position to retain the compressed spring for the first needle slide, and is configured to provide increasing resistance to depression, up until a predetermined position, at which point, the resistance is sharply increased and further depression results in the immediate release of the compressed spring. No means are provided for preventing inadvertent actuation of the automatic tissue sampling apparatus.

Due to the inherently hazardous nature of the extremely sharp points of the biopsy needle and the power of the spring-loaded mechanism, it is desirable, therefore, to provide a tissue sampling apparatus which has an automatically engaging safety mechanism, which must be consciously overcome before the tissue sampling apparatus may be actuated. In addition, it may be often awkward and/or difficult to manually overcome the force of the uncompressed springs which drive the movable slides. Accordingly, it would be desirable to provide an automatic tissue sampling apparatus which may be readily prepared for use, immediately before insertion, without the need for extreme physical exertion or the use of awkward and/or specially configured tools.

The tissue sampling device embodied in U.S. Pat. No. 4,699,154 to Lindgren discloses a housing in which two slides are mounted for longitudinal movement, the slides being configured to receive the first and second handles of the first and second needles, respectively. Each of the slides is propelled by a pair of compressed springs. The rearward slide, for propelling the handle of the first needle, is propelled by springs which bear against a rear wall of the housing. The slide for the handle of the second needle is propelled by compressed springs which bear against a fixed, transversely-extending wall arranged in the housing between the forward and rear slides. Both of the slides are arranged to have a guide member extending through them. A drawbolt is operably associated with each of the slides for limited axial movement relative thereto such that when the drawbolt is pulled backward, both of the slides are simultaneously drawn against the bias of the respective springs, to a cocking position. When the cocking position is reached, retaining members associated with each of the slides engage the respective slides to retain them in their cocked positions.

In a manner similar to that discussed with regard to the PCT '00112 application, an external triggering mechanism is provided, which is actuatable by the operator to release the retaining mechanism for the slide for the first needle. Once the slide for the first needle has been propelled forward a predetermined distance, a projection on the first slide releases the retaining mechanism for the slide for the handle of the second needle, enabling it to be propelled forward by its respective springs.

One possible drawback to the tissue sampling apparatus of the Lindgren '154 patent is that it is configured so that both sets of springs are compressed, and the slides brought into their retained positions by a single pulling motion upon the drawbolt. Accordingly, the combined strengths of all of the springs must be overcome in order to cock the mechanism. Due to the substantial power stored in the springs which is necessary for the rapid operation of the tissue sampling apparatus, it may be difficult for certain operators to rapidly and easily operate the cocking mechanism. Accordingly, it would be desirable to provide an automatic tissue sampling apparatus with a built-in cocking mechanism which is readily and easily operated, and which does not require substantial strength or effort in order to arm the apparatus.

The tissue sampling device of the Lindgren '154 patent is also provided with a safety mechanism, for precluding inadvertent actuation. However, the safety mechanism is configured such that it must be positively engaged by the operator, in order to place the tissue sampling apparatus into condition that it cannot be accidentally fired. Accordingly, the effectiveness of the safety device is dependent upon the operator remembering to set the safety. It would be more desirable to provide an automatic tissue sampling apparatus which is configured with a safety device which engages automatically upon the cocking of the apparatus, and is thereby not dependent upon the operator's remembering to engage the safety. Rather, it would be desirable to configure the safety device so the operator must affirmatively disengage the safety before the tissue sampling apparatus can be actuated.

Swiss Patent No. 483 829 discloses a "gun"-shaped automatic tissue sampling apparatus, in which the springs are cocked by direct pulling force, and so suffers from the same potential drawback of requiring substantial difficulty and effort to arm the device.

U.S. Pats. Nos. 4,944,308 and 4,953,558, issued to Akerfeldt, and EPO Application No. 0 318 447 disclose an automatic tissue sampling apparatus, in which the springs for the slides for the first and second needles are cocked by rotating in a sequential manner. Tabs on the slides ride on cam surfaces to force the slides backward against the springs requiring substantial effort to operate.

In addition to the foregoing, it is well known that often during tissue sampling procedures, the quality and/or quantity of the tissue being sampled may vary from procedure to procedure.

Accordingly, it is desirable to provide a means for permitting inspection of the tissue sample, without removing the biopsy needle components from the tissue sampling apparatus. In that way, should the size or quality of the sample be inadequate, the biopsy needle may be reinserted into the very same patient for another attempt at obtaining a suitable sample. Such a sample inspection procedure would also permit access to the sample for subsequent deposit of same onto a microscope slide or other sample holding apparatus for further processing of the tissue sample.

Such prior art tissue sampling apparatus such as those disclosed in the PCT '00112 application and in the Lindgren '154 patent are known to be large, relatively heavy and complicated devices, which are also relatively costly.

It is thus an object of the present invention is to provide an improved automatic tissue sampling apparatus which is easy to load and bring into readiness for use, without undue exertion and/or complicated manipulation of its components; while providing a facilitated, positive locking, tissue sample inspection capability.

It is a further object of the "invention to provide a automatic tissue sampling apparatus which is provided with an automatically engaging safety device, which does not rely upon the operator for its effectiveness and which must be affirmatively disengaged before the tissue sampling apparatus may be actuated.

The present invention seeks, as another goal, the provision of an automatic tissue sampling apparatus which is less complicated and therefore easier and less expensive to construct, and which has a lighter construction for greater ease of operation and manipulation.

Yet another goal of the invention is to provide an automatic tissue sampling apparatus which is provided with various internal shock and sound absorbing means so as to render the apparatus quieter and less jarring in operation, so as to decrease the actual and/or perceived discomfort of the patient during the tissue sampling procedure, while ensuring better practitioner accuracy during the procedure.

In the apparatus of U.S. patent application Ser. No. 07/753,602, now U.S. Pat. No. 5,284,156, the handles of the first and second needles are borne upon separate yokes which are each configured for longitudinal reciprocating movement within a housing. Both yokes are biased toward the front of the housing and, when the device is cocked, are held in retracted positions by separate retaining means. When the apparatus is "fired", the yoke bearing the handle of the first needle moves rapidly forward, and as it approaches its forwardmost position, it approaches a central support. Resilient members on the yoke and on the central support member cause the yoke to decelerate prior to its contact with the central support. Before the resilient members can cause the yoke to "rebound" from the central support, a second "firing" button on the yoke releases the retaining means holding the yoke for the second needle. The resilient members by then have exerted sufficient force to slightly force the first yoke backward a short distance from the central support. This rebound is necessary to permit the retaining means for the second yoke to engage during subsequent cocking of the apparatus.

While the structure and mode of operation of the automatic tissue sampling apparatus of application Ser. No. 07/753,602, now U.S. Pat. No. 5,284, 156, represents a substantial improvement over the prior art in terms of shock and noise reduction, as well as with respect to ease and safety of operation, some jarring may still exist during operation and, as a general matter, it is always desirable to seek to improve on the performance of such a device, to reduce such jarring to both improve a patient's physical and psychological well-being, and as well to further improve upon the effectiveness of the device in retrieving tissue samples.

Tissue sampling apparatus which have rearwardly positioned actuation buttons may require that the operator reposition his/her grip, since it is often the situation that the apparatus is grasped at a forward end during placement of the needle in the patient. As a further object of the invention, it is desired to provide an automatic tissue sampling apparatus which has a firing member which is accessible without requiring repositioning of the operator's grip prior to actuation of the apparatus.

It is an additional object of the invention to provide an improved automatic tissue sampling apparatus which is provided with means to facilitate rapid initial deployment of the biopsy needle system, combined with means to provide for smoother deceleration of the moving components, so as to additionally reduce shock and noise during operation.

It is an additional object of the invention to provide an improved automatic tissue sampling apparatus which provides for extended exposure of the tissue holding region, so as to provide for improved quantity and quality of tissue sample retrieved.

These and other objects and goals of the invention will become apparent and light of the present Specification, Drawings and Claims.

SUMMARY OF THE INVENTION

The present invention is directed to an automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle, and a second needle having a hollow shaft, a cutting point disposed at one end of the hollow shaft, a second handle with a passageway arranged therethrough for reciprocation of the first needle, and particularly for the automated and facilitated handling and operation of the double needle biopsy needle system during a biopsy procedure.

The automatic tissue sampling apparatus comprises a housing means which has a forward region, a rearward region, a longitudinal axis and a transverse axis. First transport means are operably disposed in the housing means, for reciprocating movement between a first transport means forward position, through an intermediate position to a first transport means retracted position, within the rearward region, in a direction substantially parallel to the longitudinal axis of the housing means. Second transport means are operably disposed in the forward region of the housing means for reciprocating movement between a second transport means forward position and a second transport means retracted position, within the forward region, in a direction substantially parallel to the longitudinal axis of the housing means. The first transport means and the second transport means are configured to receive and longitudinally move in the reciprocating directions, the first handle of the first needle and the second handle of the second needle, respectively.

First biasing means are operably arranged in the rearward region of the housing means for biasing the first transport means, and, in turn, the first needle forwardly toward the first transport means forward position. The second biasing means are operably arranged in the forward region of the housing means, for biasing the second transport means, and, in turn, the second needle forwardly toward the second transport means forward position.

Cocking means, integrally and operably associated with the first transport means and the second transport means, draw the first transport means, and, in turn, the first needle, rearwardly into the first transport means retracted position, and also draw the second transport means, and, in turn, the second needle, rearwardly into the second transport means retracted position.

First transport retaining means, operably associated with the first transport means, releasably retain the first transport means in the first transport means retracted position.

Second transport retaining means, operably associated with the second transport means, releasably retain the second transport means in the second transport means retracted position.

First release means are operably associated with the first transport retaining means, and actuate the first transport retaining means to release the first transport means from the first transport means retracted position to, in turn, enable the first transport means to be driven rapidly forward by the first biasing means, toward the first transport means forward position. Second release means, operably associated with the second transport retaining means, actuate the second transport retaining means to release the second transport means, when the first transport means is between the intermediate position and the first transport means forward position, to, in turn, enable the second transport means to be driven forward by the second biasing means.

The preferred embodiment of the invention also includes automatic tissue sample inspection means which enable the facilitated reorientation of the second transport means relative to the first transport means, after removal of the biopsy needle system from the tissue being sampled; with the first transport means, and, in turn, the first needle, in the intermediate position in the rearward region, and with the second transport means, and the second needle, repositioned in the second transport means retracted position—thereby exposing the tissue holding region and the sampled tissue which had been removed as a result of the tissue sampling procedure.

In the preferred embodiment of the invention, means are provided for rearwardly displacing the first transport means, from the first transport means forward position, to the intermediate position, as the second transport means approaches the second transport means retracted position, during the first actuation of the cocking means. The means for rearwardly displacing the first transport means preferably includes a rearwardly projecting horizontal member, operably disposed upon the second transport means, and resilient reception means operably disposed substantially within a forward facing portion of the first transport means.

The housing means comprises a substantially solid-walled, generally continuous apparatus enclosure having a substantially rectangular cross-sectional configuration for substantially enclosing all of the moving portions of the automatic tissue sampling apparatus to protect it from dirt, moisture and the like, as well as to provide audio isolation of the moving portions while reducing noise produced during operation of the apparatus. The housing means are formed by two oppositely disposed sidewalls which extend substantially parallel to the longitudinal axis. Each of the sidewalls has a forward end and a rearward end. A forward wall extends substantially parallel to the transverse axis and operably connects the forward ends of the sidewalls. A rearward wall extends substantially parallel to the transverse axis and operably connects the rearward ends of the sidewalls. A central support member is operably positioned between the sidewalls and substantially centrally between the forward and rearward walls. A bottom wall further helps to enclose the moving portions of the apparatus, while an openable cover permits the installment and removal of a biopsy needle system, yet provides full enclosure of its elements during the biopsy procedure.

In the preferred embodiment of the invention, the first and second biasing means may be operably disposed and configured to function substantially independently of each other.

The automatic tissue sample inspection means cooperates with the second transport retaining means to releasably, yet positively maintain the second transport means in the second transport means retracted position; to expose the tissue holding region with its removed sample of tissue.

Preferably, the automatic tissue sample inspection means comprises a detent member which is operably disposed on the first transport means to disengage the first transport means from the cocking means. An engagement member, operably disposed on the second transport means, places the detent member, which is normally biased into a disengaged position relative to the cocking means, into engagement with the cocking means, when the second transport means is in the second transport means retracted position.

The engagement member places the detent member into engagement with the cocking means, during actuation of the cocking means, and upon further actuation of the cocking means, the first transport means is drawn into the first transport means retracted position, within the rearward region, and retained by the first transport retaining means. At that time, re-sampling of the tissue, if necessary, may be accommodated.

The first transport means preferably comprises a first yoke member, which is longitudinally slidably retained in the rearward region, between the sidewalls, the rearward wall and the central support member. The first yoke member receives and retains the first handle of the first needle. The second transport means similarly comprises a second yoke member, which is longitudinally slidably retained in the forward region, between the sidewalls, the forward wall and the central support member, and is operably configured to receive and retain the second handle of the second needle.

In the preferred embodiment of the invention, the first biasing means is a compressed spring, operably positioned substantially between the rearward wall and the first yoke member. Likewise, a compressed spring, operably positioned substantially between the central support member and the second yoke member, forms the second biasing means.

The cocking means are so configured that when actuated, the second transport means are oriented to the second transport means retracted position, and the first transport means are oriented to the intermediate position. Further actuation of the cocking means further orients the first transport means from the intermediate position to the first transport means retracted position, placing the apparatus into readiness for projection of the needle system into the tissue to be sampled.

The cocking means preferably includes a shaft which extends substantially parallel to the longitudinal axis and is operably disposed for reciprocating movement parallel to the longitudinal axis. The shaft has two opposite ends, the first of which extends through an aperture in the rearward wall. A lever, which is disposed upon the rearward wall for pivotal movement around an axis extending substantially parallel to the transverse axis, is operably associated with the first end of the shaft such that when the lever is pivotally moved, the shaft is moved rearwardly. A cross member, operably disposed upon the second end of the shaft, engages the second yoke member, so that when the lever is actuated and the second yoke member is in its forward position, the cross member draws the second yoke member toward its retracted position.

Safety means additionally may be operably associated with at least the first release means and the cocking means to preclude inadvertent actuation of the automatic tissue sampling apparatus, once it has been cocked. The safety means preferably comprises a stop member, which is operably configured to be automatically deployed and removably positioned to physically preclude actuation of at least the first release means, upon and by actuation of the cocking means.

The present invention particularly comprises an automatic tissue sampling apparatus, having a front firing feature for a greatly facilitated use of the device. This embodiment is likewise for use with a biopsy needle system of the kind including a first needle having a shaft member and two ends, a first handle disposed at one end of the shaft member, a cutting point disposed at the other end of the shaft member, and a tissue holding region positioned between the cutting point and the first handle, and a second needle having a hollow shaft, a cutting point disposed at one end of the hollow shaft, a second handle with a passageway arranged therethrough for reciprocation of the first needle.

The automatic tissue sampling apparatus, in particular, comprises a housing; handle contacting means, operably disposed in the housing, for receiving and contacting the first and second handles of the first and second needles, toward moving same; and propulsion means, operably disposed in the housing, for moving the handle contacting means within the housing, so as to move the needle handles to expose and subsequently cover, the tissue holding region, when the biopsy needle system has been positioned at a desired location within a tissue to be sampled, the propulsion means being operably biased so as to tend to move the handle contacting means so as to expose and subsequently cover the tissue holding region, unless the handle contacting means are restrained.

The automatic tissue sampling apparatus also comprises cocking means, for placing the handle contacting means, and, in turn, the first and second needles of the biopsy needle system into suitable respective positions within the housing for subsequent movement by the propulsion means; retaining means, for holding the handle contacting means, and, in turn, the first and second needles of the biopsy needle system in the suitable respective positions within the housing, prior to actuation of the apparatus; and release means, for actuating the retaining means, so as to release the handle contacting means and enable the propulsion means to move the first and second needles, so as to expose, and subsequently cover the tissue holding region.

The release means include a front firing member operably positioned on a forward portion of the housing. The apparatus is actuatable by actuation of the front firing member.

In an alternative embodiment, the automatic tissue sampling apparatus further includes a rear firing member operably positioned on a rearward portion of the housing, the apparatus being actuatable by actuation of either of the front and rear firing members, upon cocking and desired positioning of the automatic tissue sampling apparatus.

The handle contacting means includes first and second transport means for receiving the first and second handles of the first and second needles, respectively. The propulsion means are operably configured to move at least one of the first and second transport means, so as to expose and subsequently cover the tissue holding region. The release means further comprises a movable retaining member, operably associated with at least one of the first and second transport means, for holding the at least one of the first and second transport means in the suitable position, prior to release by the release means. The movable retaining member is operably associated with at least the front firing member, so as to be moved upon movement of at least the front firing member.

In a preferred embodiment, the housing has a front face, a rear face, a top, a bottom, and two opposed side walls, and the front firing member is operably disposed in the front face of the housing. In addition, the front face has a recess operably disposed therein, and the front firing member is operably disposed in the recess such that actuation of the apparatus can be obtained only upon pressing of the front firing member into the recess.

In an alternative embodiment wherein the housing has a front face and a rear face, the apparatus has front and rear firing members, operably disposed in the front and rear faces, respectively. The front and rear firing members each extend inwardly into an interior region of the housing.

A movable retaining member, operably associated with the handle contacting means, may be operably disposed in the housing, for receiving and retaining the first and second handles of the first and second needles for holding the handle contacting means in the suitable position, prior to release by the release means. An interconnection member may be operably arranged within the housing and operably connected to the movable retaining member, so as to move substantially in conjunction with the movable retaining member, at least the front firing member being operably connected to the interconnection member. Upon movement of at least the front firing member, the interconnection member is moved, and, in turn, the movable retaining member is moved, thereby releasing the handle contacting means.

In this just-mentioned embodiment, the movable retaining member is pivotably mounted within the housing and the interconnection member comprises a pivotably mounted member having two ends. The front firing member is operably and pivotably connected to a first of the two ends, and the movable retaining member is operably connected to a second of the two ends.

In the embodiment having both front and rear firing members, the release means further comprises a movable retaining member, operably associated with the handle contacting means, operably disposed in the housing, for receiving and retaining the first and second handles of the first and second needles for holding the handle contacting means in the suitable position, prior to release by the release means. In addition, an interconnection member is operably arranged within the housing and operably connected to the movable retaining member, so as to move substantially in conjunction with the movable retaining member. The front firing member and the rear firing member are operably connected to the interconnection member. Upon movement of either of the front firing member and the rear firing member, the interconnection member is moved, and, in turn, the movable retaining member is moved, thereby releasing the handle contacting means.

The movable retaining member is pivotably mounted within the housing and the interconnection member comprises a pivotably mounted member having two ends, the front firing member being operably and pivotably connected to a first of the two ends. The movable retaining member and the rear firing member are operably and pivotably connected to a second of the two ends.

The automatic tissue sampling apparatus having a front firing member may also include automatic tissue sample inspection means for the facilitated orientation of the handle contacting means, after removal of the biopsy needle system from the tissue being sampled, to expose the tissue holding region, and enable inspection and possible removal of tissue sampled during the tissue sampling procedure.

The automatic tissue sampling apparatus having a front firing member may also include safety means, operably associated with the retaining means, for precluding inadvertent actuation of the automatic tissue sampling apparatus, once it has been cocked. The safety means preferably comprises a stop member, which is operably configured to be automatically deployed and removably positioned to physically preclude actuation of the release means, upon and by actuation of the cocking means.

BRIEF DESCRIPTION OF THE DRAWING

FIG. 1 is a perspective view of the automatic tissue sampling apparatus, according to the preferred embodiment of the invention, having a double-needle biopsy needle system loaded therein;

FIG. 2 is a perspective view of the apparatus, according to FIG. 1, with the cover opened to show how the biopsy needle system is loaded into the apparatus;

FIG. 3 is a perspective view of the apparatus, according to FIG. 2, showing, in partial cutaway, further details of the construction of the apparatus;

FIG. 4 is a top plan view of the apparatus, according to FIG. 2;

FIG. 5 is a side elevation, in section, of the apparatus, with a biopsy needle system loaded therein, in its initial configuration prior to cocking, further showing, in enlargement, the relative positions of the needles;

FIG. 6 is a side elevation, in section, showing the apparatus according to FIG. 5 during the first cocking stroke, further showing, in enlargement, the relative positions of the handles;

FIG. 7 is a side elevation, in section, of the apparatus according to FIG. 5, showing the apparatus upon completion of the first cocking stroke and release of the cocking elements immediately thereafter, further showing, in enlargement, the relative positions of the needles;

FIG. 8 is a side elevation, in section, of the apparatus according to FIG. 5, shown during the second cocking stroke further showing, in enlargement, the relative positions of the needles;

FIG. 9 is a side elevation, in section, of the apparatus according to FIG. 5, shown fully cocked, after release of the cocking elements, and ready for insertion of the biopsy needle system into the tissue to be sampled, further showing, in enlargement, the relative positions of the needles;

FIG. 10 is a side elevation, in section, of the apparatus according to FIG. 5, shown immediately after the button has been depressed, further showing, in enlargement, the relative positions of the needles;

FIG. 11 is a side elevation of the apparatus, in section, according to FIG. 5, showing the apparatus after firing but before the yokes have returned to their initial positions, equivalent to the positions prior to cocking, further showing, in enlargement, the relative positions of the needles;

FIG. 12 is a schematic perspective view, illustrating the operation of the automatically deployed safety mechanism;

DETAILED DESCRIPTION OF THE DRAWINGS

Figure 13:
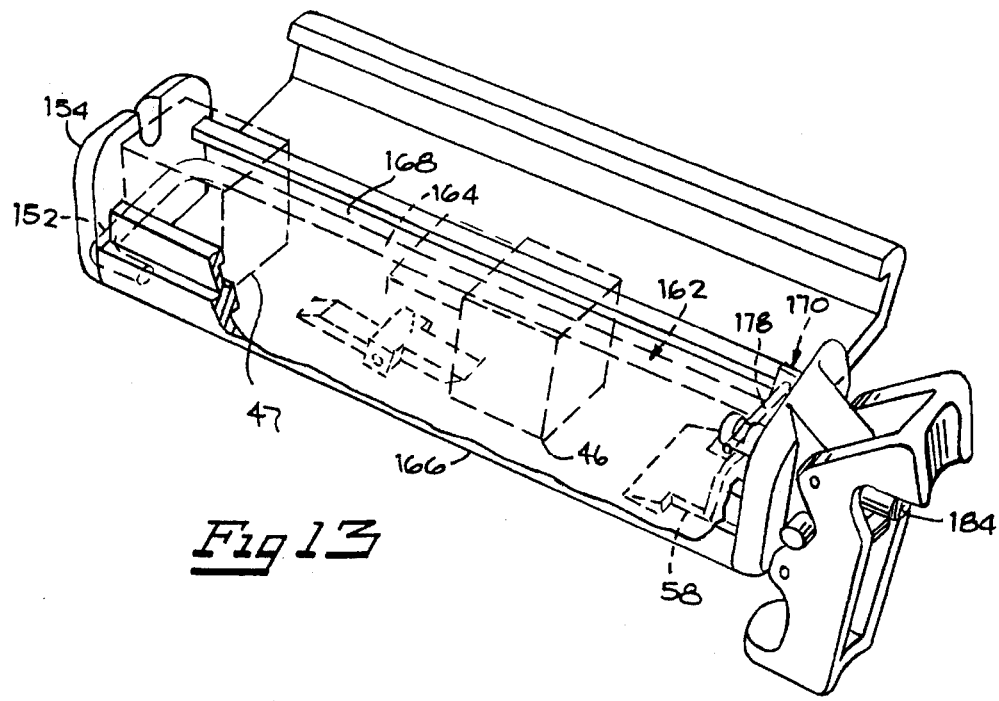
FIG. 13 is a top perspective view, in partial section, of an alternative embodiment of the apparatus, in which at least a front firing member is positioned for actuation of the apparatus.

While the present invention is susceptible of embodiment in many different forms, there is shown in the drawings and will be described herein in detail, several specific embodiments, with the understanding that the present disclosure is to be considered as an exemplification of the principles of the invention, and is not intended to limit the invention to the embodiments illustrated.

Automatic tissue sampling apparatus 20 is illustrated in FIG. 1, having biopsy needle system 22 already loaded therein. Automatic tissue sampling apparatus 20 includes housing 24 with cover 25. Automatic tissue sampling apparatus 20 is cocked using lever 28, which is provided with finger gripping portion 29 and thumb rest portion 30. Lever 28 is mounted for facilitated pivotal movement around pin 32, which is mounted in projection 33 of housing 24. Upon cocking, safety button 35 automatically shifts to one side and prevents button 36 from being inadvertently pressed. In order to enable button 36 to be depressed, safety button 35 must be pushed back in the opposite direction FIG. 2 illustrates cover 25, which, in the preferred embodiment of the invention, may be hinged to housing 24 so as to open in the manner shown. Spring catch 37 (shown in FIG. 3) holds cover 25 in the closed position, but upon moderate upward pressure to cover 25, will deflect sufficiently to release cover 25. Central support 39 is fixably mounted generally along the longitudinal center of housing 24, and generally divides the interior of housing 24 into a forward region and a rearward region. Shaft 40 is arranged for reciprocating axial movement substantially parallel to the longitudinal axis of housing 24, and is mechanically connected to lever 28 by crank 42, which is, in turn, pivotably connected to lever 28 by pin 43 and pivotably connected to shaft 40 by pin 44. Accordingly, when lever 28 is pivoted in the direction indicated by arrow A, shaft 40 moves axially backward with respect to housing 24. Yokes 46 and 47 are each configured to be retained within housing 24 by projecting tabs, such as tab 49 of yoke 46, which are received within longitudinally extending grooves, such as groove 50. Accordingly, yokes 46 and 47 are each configured to be longitudinally, slidably moved relative to support housing 24.

Shaft 40, in the preferred embodiment of the invention, is configured to pass through yokes 46 and 47, through apertures 23 and 53, respectively. Yokes 46 and 47 are each biased forwardly, with respect to housing 24, by coil springs 55 and 56, respectively. When yoke 46 is drawn toward rear wall 26 of housing 24 during cocking (as described hereinafter), it is engaged and retained adjacent rear wall 26 by retaining member 58. Retaining member 58 is normally biased to pivot in a clockwise direction around axis 59 so that engagement portions 60 of retaining member 58 are normally biased to move upwardly relative to housing 24. Engagement portions 60, which are wedge-shaped, are driven downwardly by pins 61 (as shown in FIG. 3), until pins 61 pass the rear edges of engagement portions 60, as yoke 46 approaches rear wall 26. Once pins 61 have passed the rear edges of engagement portions 60, retaining member 58 is permitted to then rotate clockwise and pins 61 abut the rear edges of engagement portions 60, preventing yoke 46 from being driven forward under the bias of now-compressed spring 55.

FIG. 3 illustrates "automatic tissue sampling apparatus 20 with yokes 46 and 47 in their fully cocked positions. Spring 62, which is weaker than either of springs 55 or 56, at one end abuts yoke 47 and at the other end abuts cross member 64. Spring 62, being at all times in a slightly compressed configuration, tends to push cross member 64 and yoke 47 apart, thereby tending to maintain shaft 40 in a forwardly drawn position with respect to, and substantially fully within, housing 24. Shaft 40 is provided with a longitudinally extending recess 65 with sharply defined end surfaces 66 and 67 as shown in FIGS. 5–11.

Yoke 47 is illustrated, in FIG. 3, in its retained position against central support 39. To draw yoke 47 against central support 39, against the bias of spring 56, when lever 28 is actuated, cross member 64 abuts the front edge of yoke 47 and forces yoke 47 backward toward central support 39. Yoke 47 is restrained in that position by retaining member 70, which is arranged for pivotal movement about axis 71. Retaining member 70 includes engagement portions 72, which engage pin 73 (see, for example, FIG. 5) in substantially the same manner as engagement portions 60 of retaining member 58 engage pins 61 of yoke 46. Retaining member 70 is, like retaining member 58, biased to pivot toward the clockwise direction (as seen in FIG. 3) and engagement portions 72 are wedge-shaped so that as yoke 47 approaches central support 39, pins 73 force retaining member 70 to pivot counter-clockwise, slightly, until pins 73 ride over and past engagement portions 72.

In order to permit the cocking of automatic tissue sampling apparatus 20, without having to overcome the combined force of both of springs 55 and 56, and as well to permit the inspection of the tissue sample once the sample has been taken (in a manner described hereinafter), the automatic tissue sampling apparatus 20 has been provided with a tissue sample inspection feature and is configured so that yokes 46 and 47 are cocked and retained against springs 55 and 56, respectively, during separate, successive actuations of lever 28. Specifically, yoke 46 is configured to normally be freely, axially movable relative to shaft 40 (aside from the biasing force of spring 55). However, catch member 74 is pivotably supported about pin 75 in a forward portion of yoke 46. Catch member 74 is biased, by spring 76, for example, in a clockwise direction upwardly away from shaft 40. However, yoke 47 is provided with rearwardly projecting pin 78 which, when yoke 47 has been drawn backward against central support 39, projects through a horizontally extending aperture (not shown) in central support 39 to depress catch member 74 downwardly toward shaft 40 so that the forwardmost edge of catch member 74 is held against the bottom of recess 65, as illustrated in FIG. 7. When lever 28 has been actuated again, the forward edge of catch member 74 abuts and is caught by the forward edge 7 of recess 65 and shaft 40, thereby pushing yoke 46 backward toward rear wall 26 and retaining member 58.

Yoke 47 additionally has rearwardly projecting pin 140 (see FIGS. 2, 3 and 4), which also is configured to pass through a horizontally extending aperture (not shown) in and extend beyond central support 39, even when yoke 47 is positioned immediately adjacent central support 39. A bore 1 41 is provided in the forward face of yoke 46, which is aligned to receive pin 140. Spring 142 is arranged to snugly fit within bore 141. The strength and stiffness of spring 142 is sufficient such that when pin 140 projects into bore 1 41, under the impulse of spring 46, spring 142 will yield slightly and then resist further compression, so that yoke 46 will be forced away from central support 39, as yoke 47 is driven to and retained substantially adjacent central support 39.

The release of yoke 46 is accomplished by pressing button 36, which pushes forward the upper end of the vertical portion of retaining member 58, simultaneously causing engagement portions 60 of retaining member 58 to pivot downwardly to remove the obstruction of pins 61 of yoke 46. Propelled by the force of spring 55, yoke 46 moves forward rapidly. Contact is first made between spring 142 in bore 141, and pin 140. Immediately, due to the stiffness of spring 142, yoke 46 begins to decelerate, although it continues to approach central support 39. As yoke 46 continues to approach central support 39, secondary button 83 contacts rearward end 84 of retaining member 70. When pushed by secondary button 83, retaining member 70 pivots against the bias of spring 79 (as shown in FIGS. 5–11 ), causing engagement portions 72 of retaining member 70 to remove the obstruction of pins 73 of yoke 47. Yoke 47 is thereby released, and is propelled by spring 56 toward the front end of apparatus 20. Substantially simultaneously, the forward face of yoke 46 encounters bumper 80. As yoke 47 recedes, the reactive force produced by the combination of pin 140 and spring 142 is lessened, and yoke 46 is brought to a smooth halt against bumper 80, with no rebound, and significantly reduced noise and jarring. Accordingly, when button 36 is pressed, yokes 46 and 47 are released consecutively in rapid succession.

It has been noted that the apparatus of the present invention provides the additional advantage of a slightly prolonged exposure of the tissue holding region, as compared to the apparatus disclosed in Ser. No. 07/753,602, now U.S. Pat. No. 5,284,156. This slightly prolonged exposure, together with the still further reduction in during sampling, and permits a greater volume of tissue to occupy the tissue holding region, before capture, resulting in greater accuracy of location and an improved tissue sample.

As previously mentioned, the automatic tissue sampling apparatus 20 of the present invention is configured to be used with a conventional two-needle biopsy needle system 22, the general configuration of which is well known and substantially consistent from manufacturer to manufacturer. Biopsy needle system 22 is composed of two parts, first needle 86 and second needle 96. First needle 86 consists of substantially solid shaft 87 with integrated handle 88. Angled point 89 is positioned at the end of shaft 87, opposite from handle 88, to facilitate insertion of the needle system into the tissue to be sampled. Proximate to point 89, tissue holding region 90 is cut-out from shaft 87, as illustrated in FIG. 6. When biopsy needle system 22 is inserted into a tissue to be sampled, and tissue holding region 90 is exposed, a portion of the tissue moves into tissue holding region 90, and is sheared off and retained there as the desired sample.

Shaft 87 is freely inserting received by hollow shaft 97 of second needle 96, with integrated handle 98. An aperture (not shown) extends through the length of handle 98. Handles 88 and 98 are typically additionally configured to be asymmetrical, particularly with tabs 92, and 99a and 99b, which have portions projecting perpendicularly from handles 88 and 98, respectively. As the length of shaft 87 exceeds the combined length of hollow shaft 97 and handle 98, point 89, at substantially all times during normal use, is exposed. The foregoing biopsy needle system description is typical of biopsy needle systems, though the particular contours, proportions configurations and handle shapes, though not handle size, may vary somewhat from one manufacturer to another. However, the principles of the automatic tissue sampling apparatus of the present invention are applicable to all.

The operation of biopsy needle system 22, to obtain and retrieve a tissue sample, is as follows. When point 89 is inserted into a tissue, first needle 86 and second needle 96 must be in the configuration shown in FIG. 5, that is, with second needle 86 moved forwardly relative to first needle 86, so that hollow shaft 97 covers tissue holding region 90 of shaft 87, but point 89 remains forwardmost and exposed.

Once first needle 86 and second needle 96 have been inserted into the tissue, first needle 86 is moved forward, with respect to second needle 96, further into that particular region of the tissue, from which a sample is to be retrieved. During this step, second needle 96 is to be stabilized, with respect to the patient and the tissue, for accuracy and for the comfort of the patient.

As point 89 of first needle 86 proceeds further into the tissue, tissue holding region 90 becomes exposed. Since the tissue is not a rigid medium, a portion of the tissue "flows" to fill in, at least partially, tissue holding region 90. To retrieve and remove the sample, second needle 96 is then rapidly thrust forward, relative to first needle 86, which, in turn, is stabilized relative to the patient and the tissue—to eventually shear off and enclose the tissue that had previously flowed into tissue holding region 90.

As illustrated in FIGS. 5 through 11, hollow shaft 97 is also provided with point 100, which is also angled so that the extreme tip 101 of point 100 is positioned, when first needle 86 and second needle 96 are aligned, on the side of the shaft 15 in which tissue holding region 90 is formed. Proper alignment of first needle 86 and second needle 96 is obtained when the projecting portions of tabs 92, 99a and 99b are aligned.

Accordingly, as second needle 96 is moved forward relative to first needle 86, extreme tip 101 cuts the tissue to leave a portion of the tissue within tissue holding region 90. As second needle 96 continues to move forward, the tissue sample and tissue holding region 90 are covered. At this point, first needle 86 and second needle 96 have resumed the relative positions indicated by FIG. 5 and must be withdrawn from the patient together in that position, in order to prevent the tissue sample from being dislodged or contaminated by other tissue.

To accomplish such operations with precision, speed and a minimum of discomfort to the patient, using manual methods, is extremely difficult. Automatic tissue sampling apparatus 20 enables the foregoing procedure to be accomplished swiftly, with a substantially reduced level of discomfort to the patient, and with a high degree of repeatability of result from one procedure to the next.

FIGS. 5 through 11 illustrate the successive steps in the operation of the automatic tissue sampling apparatus 20. In FIG. 5, automatic tissue sampling apparatus 20 is shown in an uncocked configuration. Hollow shaft 97 of second needle 96 covers tissue holding region 90 of first needle 86. A first actuation of lever 28 causes cross member 64 to abut the front face yoke 47, driving yoke 47 against the force of spring 56, into position to be retained by retaining member 70. This procedure draws second needle 96 backward relative to first needle 86, thus exposing tissue holding region 90. As previously described, once yoke 47 has been drawn back and retained by retaining member 70, pin 78 depresses catch member 74 against the bias of spring 76. Accordingly, when lever 28 is returned to its lowered position, returning shaft 40 to its fully forward position, catch member 74 is forced into recess 65.

In addition, during the first actuation of lever 28, as yoke 47 approaches central support 39, pin 140 passes through central support 39 and contacts spring 142 within bore 141. Spring 142 compresses slightly and then resists further compression, causing yoke 46 to be forced away from central support 39, as described earlier.

A subsequent actuation of lever 28, again draws back shaft 40. However, leading edge 67 of recess 65 pushes on catch member 74 to force yoke 46 further backward toward retaining member 58. The upper end of retaining member 58 simultaneously pushes button 36 backward relative to rearward projecting portion 33 of housing 24. Returning lever 28 to its initial position again places automatic tissue sampling apparatus 20 into a configuration ready for insertion of biopsy needle system 22 into the tissue to be sampled, or resampled, if required.

Due to the power and speed with which the yokes 46 and 47 are propelled forward, respectively, by springs 55 and 56, once button 36 is depressed, and in view of the hazardous nature of the biopsy needle system, it is highly desirable to provide automatic tissue sampling apparatus 20 with an automatically deployed safety mechanism to prevent actuation of automatic tissue sampling apparatus 20. The present invention is provided with such a safety mechanism, in part illustrated in FIG. 12.

FIG. 12 shows shaft 40 and safety button 35. Shaft 40 has arranged, upon an upper surface thereof, cam surface 110. Button 36 is formed in three parts, forward large diameter portion 120, central narrow portion 121, and rearward large diameter portion 122. Safety button 35 is configured as a substantially cylindrical rod having, on an upper surface thereof, an arcuate depression 111 formed thereon and extending substantially longitudinally along the axis of safety button 35. Safety button 35 is disposed parallel to the transverse axis of housing 24, for limited reciprocal movement in an aperture in projection 33. Upon the lower half of safety button 35, a recess is carved out having a depth substantially equal to the depth of cam surface 110 and having a width slightly greater than the width of shaft 40. When shaft 40 is in its forwardmost position within housing 24, as shown in FIG. 5, shaft 40 occupies the position, relative to safety button 35, indicated by the solid line button 35 in FIG. 12. As illustrated, recesses 111 and 112 are slightly offset in the transverse direction. Recess 111, when positioned relative to shaft 40 as shown in the solid line figure in FIG. 12, enables the rearward large diameter portion 122 of button 36 to pass over safety button 35, enabling button 36 to move forwardly sufficiently to pivot retaining member 58 and release yoke 46.

When lever 28 is cocked, shaft 40 is automatically moved in the direction of the arrow B in FIG. 12 and cam surface 110 forces safety button 35 to move in the direction of arrow C and thus occupy the position, relative to the shaft 40, shown as 35'. When lever 28 is returned to its lower position, shaft 40 moves forward again relative to housing 24. While recess 112 is at that time positioned over the widest part of cam surface 110, safety button 35 is held by friction in its safety position, with recess 111'offset to one side of shaft 40. Accordingly, if button 36 is depressed, the rearward large diameter portion 122 of button 36 abuts and is blocked by safety button 35. Only when safety button 35 is pushed in the direction opposite arrow C in FIG. 12, so that recess 111 again becomes aligned with shaft 40, can button 36 be fully depressed, to actuate apparatus 20.

Once biopsy needle system 22 has been positioned in the patient and into the particular tissue to be sampled, and safety button 36 moved to release button 35, automatic tissue sampling can be effectuated. FIG. 10 illustrates automatic tissue sampling apparatus 20 in a configuration only a split second after button 36 has been fully depressed. Retaining member 58 has been pivoted counter-clockwise, with engagement surfaces 60 no longer obstructing pins 61. Yoke 46 is moving rapidly toward central support 39 under the impetus of spring 55. Shaft 87 of first needle 86 is being propelled forward relative to hollow shaft 97 of second needle 96. Tissue holding region 90 is being exposed. Pin 140 connects with spring 142 (not shown in FIGS. 5–11) and causes yoke 46 to slow down in its forward movement. Yoke 46 continues forward, and secondary button 83 reaches retaining member 70 and causes it to rotate counterclockwise, as illustrated in FIG. 11. Engagement surfaces 72 of retaining member 70 clear pins 73 and thus yoke 47 is propelled forward by spring 56. Second needle 96 is brought forward so that shaft 97 covers tissue holding region 90 of first needle 86. Yoke 46 is brought to rest against bumper 80.

The first and second needles 86 and 96 respectively, are held together to facilitate removal of biopsy needle system 22 from the tissue being sampled. Once removed from the patient, it is often desirable to inspect the tissue holding region 90, in order to determine whether a sample has been successfully taken and, if so, to enable deposit of the sample onto a microscope slide, or other appropriate receptacle. Inspection of tissue holding region 90 is easily accomplished in the present invention-by merely applying a single stroke to actuating lever 28 after it has been fired, in order to draw back second needle 96, as illustrated in FIG. 6. If a suitable sample has not been retrieved, after inspection, a second actuation of lever 28 draws back first needle 86, and places the automatic tissue sample apparatus again in a fully cocked configuration, ready for the reinsertion of biopsy needle system 22 into the tissue to be sampled.

An additional advantage of the construction of the invention, is that the provision of pin 140, spring 142, and bumpers 80 and 130 prevent actual contact between yokes 46 and 47, and central support 39 and forward wall 131, which tend to reduce the noise otherwise associated with such apparatus. In addition, the deceleration produced by these elements tends to reduce the "shock" which may be felt when apparatus 20 is actuated. Noise and shock are further reduced by fabricating bumpers 80 and 130 from resilient compressible plastic or rubber material, and by fabricating yokes 46 and 47 from nylon or similar materials. By reducing noise and shock, the patient's discomfort, actual and/or perceived, during the sampling procedure, will be reduced.

Figure 14:
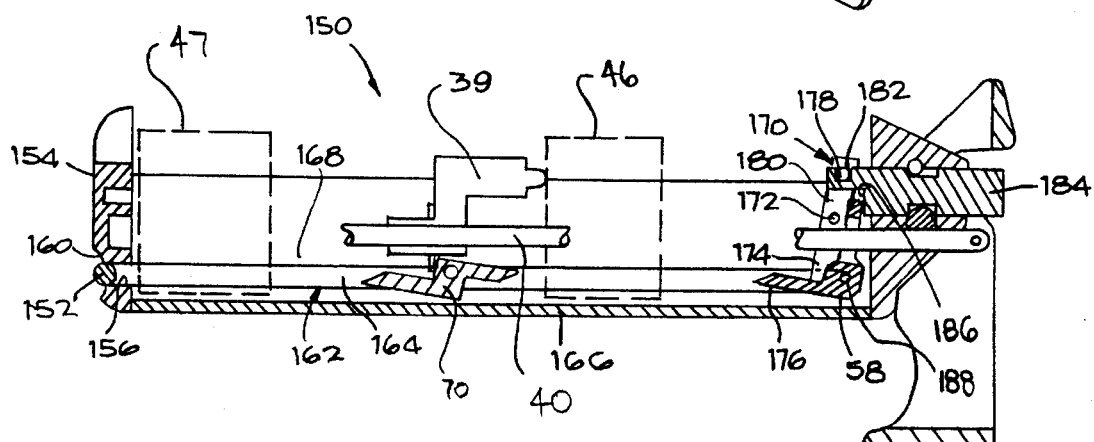
FIG. 14 is a side elevation, in partial section, of an alternative preferred embodiment of the invention, according to FIG. 13.
Figure 15:
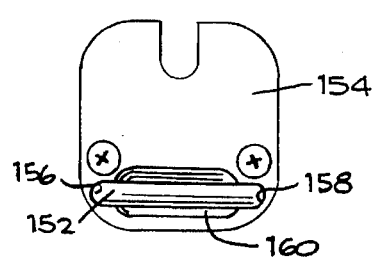
FIG. 15 is a front elevation of the apparatus shown in FIG. 13.

FIGS. 13–15 illustrate an alternative embodiment of the invention. While the previously described embodiments comprise improvements over the prior art, the alternative embodiment of FIGS. 13–15 comprises an even further improvement over the prior art. It has been observed that manipulation of the previously described embodiments can, on occasion, be complex, in that the physician or medical technician who is operating the device, typically grasps an apparatus 20 at the front end of housing 24, while the end of needle 22 is being positioned into a patient. The grasping is typically done one-handed, as the operator is typically holding an ultrasonic sender-sensor in the other hand, while observing placement of the end of needle 22 on the display of the ultrasonic device. Once the end of the needle has been positioned, then the operator must shift his grip on apparatus 20, in order to reach firing button 36 to fire apparatus 20. The shifting of the grip is not only inconvenient to the operator, it can cause shifting of the positioning of the end of the needle 22, within the patient, both compromising the accuracy of the tissue sampling, and possibly causing additional discomfort to the patient.

In yet other uses, the device is placed into a staging fixture, which grips the apparatus at various locations, and which often requires manipulation or adjustment toward the front of the apparatus.

Apparatus 150 is operably configured to alleviate the aforementioned potential problems presented by the required shifting of grip by an operator. Apparatus 150 includes a front-accessible firing button 152, which enables apparatus 150 to be fired, one-handed, or from within a staging fixture—without the operator having to shift grip after completing placement of the end of needle 22, and without inadvertent movement of the fixture. The location and recessing of the front accessible firing button 152 simultaneously avoids inadvertent actuation by the clamping elements of a staging fixture.

While in the illustrated embodiment, apparatus 150 has both rear firing pin 36 as well as front firing button 152, in yet another embodiment, rear firing pin 36 may be replaced with a shortened member which does not project outwardly from the rear of apparatus 150, such that actuation of apparatus 150 may only be accomplished by front firing button 152.

The cocking, firing and safety mechanisms disclosed in FIGS. 1–12 are present in apparatus 150, in substantially unmodified form, and so are only partially illustrated in phantom outline in FIGS. 13–15. Yokes 46 and 47 are representatively illustrated in their respective forward positions, although other constructions for contacting and propelling the handles of the needle apparatus may be employed. Apparatus 150 includes a modified front plate 154, having apertures 156 and 158, and rounded depression 160 into which firing button 152 may be depressed.

Firing button 152 is formed from the externally exposed transverse portion of J-shaped firing member 162. Longitudinal portion 164 of firing member 162 extends along the interior of housing 166 of apparatus 150, preferably in an appropriately configured channel or groove, such as channel 168, to the side and out of the way of the movable yokes, in which are to be seated the handles of the needle apparatus.

Interconnection arm 170 is pivotably mounted on pin 172. Lower end 174 of interconnection arm 170 is, in turn, pivotably connected to end 176 of firing member 162. Lateral pin 178 emanates horizontally from upper end 180 of interconnection arm 170, and is operably positioned so as to be pivotably received in lateral slot 182 in rear firing pin 184, which is otherwise configured to be substantially identical to firing pin 36 described with respect to the previous embodiment.

In this preferred embodiment, after apparatus 150 has been loaded and armed, in the manner described with respect to the previous embodiment, firing button 152 is depressed, causing longitudinal portion 164 to move backwards, away from front plate 154. The lower end 174 of interconnection arm 170 moves away from front plate 154. Interconnection arm 170 is forced to pivot, and lateral pin 178 pushes on the forward inside wall of slot 182, pushing/pulling firing pin 184 forward. Face 186 of firing pin 184 pushes against the top of retaining member 58, causing retaining member 58 to pivot about pin 188. Yoke 46 is thereafter released, and apparatus 150 is actuated in the previously described manner, identical to the manner as if firing pin 184 (36 in the previous embodiment) had been depressed.

In a preferred embodiment of the invention, there is no significant frictional resistance generated against the movement of any of firing member 162, interconnection arm 170, pin 172, or lateral pin 182, apart from that encountered directly resulting from the resistance of retaining member 58 to release the rear yoke.

It is believed that apparatus 150, which may be fired either with front firing button 152, or, if rear firing pin 184 is provided, rear firing pin 184, provides an improved operation, particularly for those operators who may grasp apparatus 150 either manually or in a fixture, along the front of housing 166, in that front firing button 152 enables actuation of apparatus 150, without the need of the operator to reposition his/her grip, before firing. Firing button 152, in a preferred embodiment of the invention, is positioned within rounded depression 160, so as to be substantially flush with the face of front plate 154, so that, when apparatus 150 is armed, a positive inward pushing movement is required to fire apparatus 150, and the likelihood of accidental firing, such as by contact with a flat surface, from the fixture or otherwise, is substantially reduced.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle, and a second needle having a hollow shaft, a cutting point disposed at one end of the hollow shaft, a second handle with a passageway arranged therethrough for reciprocation of the first needle, said automatic tissue sampling apparatus comprising:

a housing;

handle contacting means, operably disposed in said housing, for receiving and contacting said first and second handles of said first and second needles, toward moving same;

propulsion means, operably disposed in said housing, for moving said handle contacting means within said housing, so as to move said needle handles to expose and subsequently cover, said tissue holding region, when said biopsy needle system has been positioned at a desired location within a tissue to be sampled, said propulsion means being operably biased so as to tend to move said handle contacting means so as to expose and subsequently cover said tissue holding region, unless said handle contacting means are restrained;

cocking means, for placing said handle contacting means, and, in turn, said first and second needles of said biopsy needle system into suitable respective positions within said housing for subsequent movement by said propulsion means;

retaining means, for holding said handle contacting means, and, in turn, said first and second needles of said biopsy needle system in said suitable respective positions within said housing, prior to actuation of said apparatus;

release means, for actuating said retaining means, so as to release said handle contacting means and enable said propulsion means to move said first and second needles, so as to expose, and subsequently cover said tissue holding region, said release means including
a front firing member operably positioned on a forward portion of said housing,
said apparatus being actuatable by actuation of said front firing member; and
means for substantially precluding inadvertent actuation of said front firing member.

2. The automatic tissue sampling apparatus according to claim 1, further comprising:
a rear firing member operably positioned on a rearward portion of said housing,
said apparatus being actuatable by actuation of either of said front and rear firing members, upon cocking and desired positioning of said apparatus.

3. The automatic tissue sampling apparatus according to claim 1 wherein said handle contacting means includes first and second transport means for receiving said first and second handles of said first and second needles, respectively, and said propulsion means are operably configured to move at least one of said first and second transport means, so as to expose and subsequently cover said tissue holding region, and said release means further comprises:
a movable retaining member, operably associated with at least one of said first and second transport means, for holding said at least one of said first and second transport means in said suitable position, prior to release by said release means, said movable retaining member being operably associated with at least said front firing member, so as to be moved upon movement of said at least said front firing member.

4. The apparatus according to claim 1, wherein said housing has a front face, a rear face, a top, a bottom, and two opposed side walls.

5. The apparatus according to claim 1, wherein said release means further comprises:
a movable retaining member, operably associated with said handle contacting means, operably disposed in said housing, for receiving and retaining said first and second handles of said first and second needles for holding said handle contacting means in said suitable position, prior to release by said release means,
an interconnection member, operably arranged within said housing and operably connected to said movable retaining member, so as to move substantially in conjunction with said movable retaining member, at least said front firing member being operably connected to said interconnection member, such that upon movement of said at least said front firing member, said interconnection member is moved, and, in turn, said movable retaining member is moved, thereby releasing said handle contacting means.

6. The apparatus according to claim 5, wherein said movable retaining member is pivotably mounted within said housing and said interconnection member comprises a pivotably mounted member having two ends, said front firing member being operably and pivotably connected to a first of said two ends, and said movable retaining member being operably and pivotably connected to a second of said two ends.

7. The apparatus according to claim 2, wherein said release means further comprises:
a movable retaining member, operably associated with said handle contacting means, operably disposed in said housing, for receiving and retaining said first and second handles of said first and second needles for holding said handle contacting means in said suitable position, prior to release by said release means,
an interconnection member, operably arranged within said housing and operably connected to said movable retaining member, so as to move substantially in conjunction with said movable retaining member, said front firing member and said rear firing member being operably connected to said interconnection member, such that upon movement of either of said front firing member and said rear firing member, said interconnection member is moved, and, in turn, said movable retaining member is moved, thereby releasing said handle contacting means.

8. The apparatus according to claim 7, wherein said movable retaining member is pivotably mounted within said housing and said interconnection member comprises a pivotably mounted member having two ends, said front firing member being operably and pivotably connected to a first of said two ends, and said movable retaining member and said rear firing member being operably and pivotably connected to a second of said two ends.

9. The apparatus according to claim 1, further comprising:
automatic tissue sample inspection means for the facilitated orientation of the handle contacting means, after removal of the biopsy needle system from the tissue being sampled, to expose the tissue holding region, and enable inspection and possible removal of tissue sampled during the tissue sampling procedure.

10. The apparatus according to claim 1, further comprising:
safety means, operably associated with said retaining means, for precluding inadvertent actuation of the automatic tissue sampling apparatus.

11. The apparatus according to claim 10, wherein said safety means comprises a stop member, operably configured to be automatically deployed and removably positioned to physically preclude actuation of said release means, upon and by actuation of said cocking means.

12. The apparatus according to claim 1, wherein said front firing member is operably disposed in a front face of said housing.

13. The apparatus according to claim 12, wherein said means for substantially precluding inadvertent actuation of said front firing member comprises a recess operably disposed in said front face, and said front firing member is operably disposed in said recess such that actuation of said apparatus can be obtained only upon pressing of said front firing member into said recess.

14. The apparatus according to claim 2, wherein said housing has a front face and a rear face, and said front and rear firing members being operably disposed in said front and rear faces, respectively.

15. The apparatus according to claim 14, wherein said front and rear firing members each project inwardly into an interior region of said housing.

16. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle, and a second needle having a hollow shaft, a cutting point disposed at one end of the hollow shaft, a second handle with a passageway arranged therethrough for reciprocation of the first needle, said automatic tissue sampling apparatus comprising:

a housing;

handle contacting means, operably disposed in said housing, for receiving and contacting said first and second handles of said first and second needles, toward moving same;

propulsion means, operable disposed in said housing, for moving said handle contacting means within said housing, so as to move said needle handles to expose and subsequently cover, said tissue holding region, when said biopsy needle system has been positioned at a desired location within a tissue to be sampled, said propulsion means being operably biased so as to tend to move said handle contacting means so as to expose and subsequently cover said tissue holding region, unless said handle contacting means are restrained;

cocking means, placing said handle contacting means, and, in turn, said first and second needles of said biopsy needle system into suitable respective positions within said housing for subsequent movement by said propulsion means;

retaining means, for holding said handle contacting means, and, in turn, said first and second needles of said biopsy needle system in said suitable respective positions within said housing, prior to actuation of said apparatus;

release means, for actuating said retaining means, so as to release said handle contacting means and enable said propulsion means to move said first and second needles, so as to expose, and subsequently cover said tissue holding region, said release means including
a front firing member operably positioned on a forward portion of said housing,
said apparatus being actuatable by actuation of said front firing member,
said front firing member further being operable disposed in a front face of said housing.

17. The apparatus according to claim 16, wherein said front face has a recess operably disposed therein, and said front firing member is operably disposed in said recess such that actuation of said apparatus can be obtained only upon pressing of said front firing member into said recess.

18. An automatic tissue sampling apparatus, for use with a biopsy needle system of the kind including a first needle having a shaft member and two ends, a first handle disposed at one end of the shaft member, a cutting point disposed at the other end of the shaft member, and a tissue holding region positioned between the cutting point and the first handle, and a second needle having a hollow shaft, a cutting point disposed at one end of the hollow shaft, a second handle with a passageway arranged therethrough for reciprocation of the first needle, said automatic tissue sampling apparatus comprising:

a housing;

handle contacting means, operably disposed in said housing, for receiving and contacting said first and second handles of said first and second needles, toward moving same;

propulsion means, operably disposed in said housing, for moving said handle contacting means within said housing, so as to move said needle handles to expose and subsequently cover, said tissue holding region, when said biopsy needle system has been positioned at a desired location within a tissue to be sampled, said propulsion means being operably biased so as to tend to move said handle contacting means so as to expose and subsequently cover said tissue holding region, unless said handle contacting means are restrained;

cocking means, for placing said handle contacting means, and, in turn, said first and second needles of said biopsy needle system into suitable respective positions within said housing for subsequent movement by said propulsion means;

retaining means, for holding said handle contacting means, and, in turn, said first and second needles of said biopsy needle system in said suitable respective positions within said housing, prior to actuation of said apparatus;

release means, for actuating said retaining means, so as to release said handle contacting means and enable said propulsion means to move said first and second needles, so as to expose, and subsequently cover said tissue holding region, said release means including
a front firing member operably positioned on a forward portion of said housing,
said apparatus being actuatable by actuation of said front firing member;
a rear firing member operably positioned on a rearward portion of said housing,
said apparatus being actuatable by actuation of either of said front and rear firing members, upon cocking and desired positioning of said apparatus,
said housing further having a front face and a rear face, and said front and rear firing members are operably disposed in said front and rear faces, respectively.

19. The apparatus according to claim 18, wherein said front and rear firing members each extend inwardly into an interior region of said housing.

* * * * *

UNITED STATES PATENT AND TRADEMARK OFFICE
CERTIFICATE OF CORRECTION

PATENT NO. : 5,507,298
DATED     : April 16, 1996
INVENTOR(S) : Schramm et al.

It is certified that error appears in the above-indentified patent and that said Letters Patent is hereby corrected as shown below:

Col. 21, line 45  Delete "placing" and insert instead -- for placing --.

Signed and Sealed this

Third Day of August, 1999

Q. TODD DICKINSON

*Attest:*

*Attesting Officer*    *Acting Commissioner of Patents and Trademarks*